(12) United States Patent
Shiga et al.

(10) Patent No.: US 7,366,565 B2
(45) Date of Patent: Apr. 29, 2008

(54) EXERCISE MACHINE, PHYSICAL STRENGTH EVALUATION METHOD AND PULSE RATE METER

(75) Inventors: Toshikazu Shiga, Otsu (JP); Tatsuya Kobayashi, Otsu (JP); Hiromi Matsumoto, Kyoto (JP); Manabu Yoshimura, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 798 days.

(21) Appl. No.: 10/310,176

(22) Filed: Dec. 5, 2002

(65) Prior Publication Data

US 2003/0149371 A1 Aug. 7, 2003

Related U.S. Application Data

(62) Division of application No. 09/622,933, filed as application No. PCT/JP99/00829 on Feb. 24, 1999, now Pat. No. 6,512,948.

(30) Foreign Application Priority Data

Feb. 26, 1998 (JP) .................................. 10-45705
Feb. 27, 1998 (JP) .................................. 10-46803

(51) Int. Cl.
*A61B 5/0402* (2006.01)

(52) U.S. Cl. ..................................................... 600/520
(58) Field of Classification Search ............... 600/519, 600/520; 428/8, 57, 66
See application file for complete search history.

(56) References Cited

U.S. PATENT DOCUMENTS 3,845,756 A * 11/1974 Olsson ........................ 600/520
4,337,529 A 6/1982 Morokawa
5,297,558 A * 3/1994 Acorn et al. ................. 600/532
5,301,154 A 4/1994 Suga (Continued)

FOREIGN PATENT DOCUMENTS

DE 42 28 091 A1 3/1994

(Continued)

OTHER PUBLICATIONS

Supplementary Partial European Search Report dated Jul. 23, 2004.

(Continued)

*Primary Examiner*—Carl Layno
*Assistant Examiner*—Frances P. Oropeza
(74) *Attorney, Agent, or Firm*—Morrison & Foerster LLP

(57) ABSTRACT

In an exercise machine, when a measurement starts, an electrocardiographic signal is detected by an electrocardiographic sensor 1 (ST33), a load drive is started (ST4), and heartbeat rate intervals of the electrocardiographic signal are sequentially obtained. A fluctuation of heartbeat rate intervals PI(n) % is obtained from a calculation formula in which the RR interval RR(n+1) of the current heartbeat is subtracted from the RR interval RR(n) of the previous heartbeat, which is then divided by RR(n) and multiplied by 100% (ST5). Entropy is calculated from 128 pieces of such PI (ST6). From the change of the entropy under the gradually increasing load (ST8), a minimum point of the entropy is obtained, which point is designated as an anaerobic threshold point (ST7). The load of the exercise machine is controlled employing this anaerobic threshold.

2 Claims, 18 Drawing Sheets

U.S. PATENT DOCUMENTS

| | | | |
|---|---|---|---|
| 5,410,472 A | * | 4/1995 | Anderson ............ 482/9 |
| 5,527,239 A | | 6/1996 | Abbondanza |
| 5,840,039 A | | 11/1998 | Heikkila |
| 6,104,947 A | * | 8/2000 | Heikkila et al. ............ 600/519 |
| 6,301,499 B1 | | 10/2001 | Carlson et al. |

FOREIGN PATENT DOCUMENTS

| EP | 0 255 621 | 2/1988 |
|---|---|---|
| EP | 0 379 227 | 7/1990 |
| EP | 0 569 879 A2 | 11/1993 |
| EP | 0688533 A1 | 5/1995 |
| EP | 0761163 A2 | 3/1997 |
| EP | 0842635 A1 | 5/1998 |
| JP | 7-38885 | 5/1995 |
| JP | 07-116286 | 5/1995 |
| JP | 08-084755 | 4/1996 |
| JP | 10-137362 | 5/1998 |
| WO | WO 96/11630 | 4/1996 |
| WO | 96/20640 | 7/1996 |
| WO | WO-96/20640 A1 | 7/1996 |

OTHER PUBLICATIONS

The 53rd Annual Meeting of the Japanese Society of Physical Fitness and Sports Medicine, 1998, Lecture No. 252.
Journal of Sports & Science, vol. 7, No. 1, 1993, pp. 31-39.
The American Physiological Society, 1991, pp. 1136-1142.
The American Physiological Society, 1997, pp. 1794-1800.
Notice of Ground of Rejection of JP 2000-533182 dated Apr. 8, 2003.

* cited by examiner

EXERCISE MACHINE, PHYSICAL STRENGTH EVALUATION METHOD AND PULSE RATE METER

REFERENCE TO RELATED APPLICATIONS

This application is a divisional of Ser. No. 09/622,933, filed Aug. 24, 2000 now U.S. Pat. No. 6,512,948, which is a national stage application, under 35 USC 371, of PCT/JP99/00829, filed Feb. 24, 1999.

The prior applications, in their entirety, are hereby incorporated by reference.

TECHNICAL FIELD

The present invention relates to an exercise machine, such as bicycle ergometer, treadmill and rowing ergometer, a physical strength evaluation method and a pulse rate meter.

BACKGROUND ART

Method and apparatus for determining exertion levels interested in this invention are disclosed, for example, in International Publication No. WO96/20640. According to the disclosure, heartbeat of a person engaged in training is monitored. From an electrocardiographic signal obtained, a QRS complex waveform, for example, is measured to calculate the heartbeat rate. Based on a power of a spectrum derived from the heartbeat rate, an exertion level of the exercising person is determined.

Further, conventional method and apparatus for measuring muscular endurance of a person engaged in exercise are disclosed, for example, in Japanese Patent Publication No. 7-38885. According to the disclosure, a load of an exercising person is calculated from the product of a heartbeat rate and a blood pressure under vasoconstriction, and from the result, the muscular endurance is calculated.

The load of a person engaged in training or exercise has conventionally been measured as described above. Such measurement has also made it possible to estimate the load of an exercising person.

Conventionally, exercise machines such as a bicycle ergometer and others have been commercially available for health maintenance and enhancement. In some of such exercise machines, a person inputs his/her age, sex and the like, and an exercise program is arranged according to such information based on statistically predetermined exertion intensity. For evaluation of a physical strength level, some machines have adapted a method of estimating the maximum oxygen intake based on a change of pulsation or the like corresponding to a change of exertion load.

There is a factor for decision of safe and effective exercise; i.e., an anaerobic threshold (hereinafter, also referred to as "AT"). This threshold value of exertion intensity shows a maximum exertion level at which exercise can be done without an abrupt increase of lactic acid in the blood. The AT is conventionally determined employing an invasive method by taking a blood sample to examine the lactic acid level, or in a restraining manner by measuring changes of oxygen and carbondioxide partial pressures in exhalation by breathing gas analysis.

Further, for evaluation of physical strength, there are conventionally known methods of estimating maximum oxygen intake, maximum exertion intensity, maximum heartbeat rate and others based on a change of pulsation or the like with respect to the exertion load.

Such conventional exercise machines and apparatuses for determining exertion levels, however, have posed the following problems:

① The data obtained from the apparatus and method for determining the exertion level has been used only physiologically to determine the exertion level in training or exercise; the data has not been utilized effectively.

② Setting of exertion intensity does not conform to working capacity of each person; a sought-after effect cannot be obtained sufficiently from the exercise.

③ Although the AT is considered most appropriate as the exertion intensity in conformity with the working capacity of the individual, measurement of the AT is restraining and requires a special apparatus such as a breathing gas analyzer; such a measuring apparatus cannot practically be mounted on an exercise machine.

④ The AT, which represents aerobic working capacity important for decision of physical strength, cannot be determined by or displayed on the exercise machine due to the reason stated in ③ above.

The present invention is directed to solve the above-described problems, and its object is to provide an exercise machine which allows an exertion level to be readily and accurately found so that the value can be used for effective training.

Another object of the present invention is to provide an exercise machine which allows an anaerobic threshold to be readily and accurately found so that the value can be used for effective training.

Yet another object of the present invention is to provide an exercise machine and a physical strength evaluating method which allow physical strength and exertion levels to be readily found at the same time, allow a user to understand his/her own working capacity in more detail to do appropriate exercise, and allow the physical strength and exertion levels to be evaluated with high precision in a time period as short as possible.

A still further object of the present invention is to provide a pulse rate meter which allows an exertion level to be readily and accurately found.

DISCLOSURE OF THE INVENTION

The exercise machine according to the present invention includes: a load device capable of changing a load; a physiological signal measuring unit measuring a physiological signal noninvasively over time; an exertion level estimating unit estimating an exertion level based on the physiological signal corresponding to the change of the load of the load device; and a unit for controlling the load of the load device employing the exertion level estimated.

The exertion level is estimated based on the physiological signal corresponding to the change of the load of the load device, and the load of the load device is controlled to come close to the estimated exertion level. Therefore, an exercise machine allowing a user to do appropriate exercise corresponding to his/her own working capacity can be provided.

Preferably, the exertion level estimating unit estimates the exertion level based on a change of the physiological signal in response to the change of the load of the load device.

More preferably, the exertion level estimating unit estimates an anaerobic threshold as the exertion level.

The exertion level estimating unit estimates the anaerobic threshold as the exertion level, and the load of the exercise machine is controlled based on this threshold value. Thus, an exercise machine allowing a user to do appropriate exercise more efficiently corresponding to his/her own working capacity can be provided.

According to an aspect of the present invention, the exertion level estimating unit includes a unit for calculating a fluctuation of heartbeat rate intervals in each electrocardiographic signal detected, a unit for calculating a power of the fluctuation of heartbeat rate intervals and a unit for finding a convergence point of a change of the power with respect to the increase of the load, and estimates an exertion load corresponding to the convergence point as the exertion level.

The fluctuation of heartbeat rate intervals in the electrocardiographic signal is calculated and the convergence point of the power change of the fluctuation with respect to the load increase is obtained to estimate the exertion level. Thus, an exercise machine capable of evaluating the exertion level with high precision in a short time period can be provided.

According to another aspect of the present invention, the exercise machine includes: a load device gradually increasing a load over time; an electrocardiographic sensor detecting an electrocardiographic signal; a unit for measuring a heartbeat rate of the electrocardiographic signal detected while the load is gradually increased; a unit for calculating a fluctuation of heartbeat rate intervals in the electrocardiographic signal; an exertion level estimating unit estimating an exertion level based on the heartbeat rate and the fluctuation of heartbeat rate intervals; a unit for estimating physical strength based on a slope of the change of the heartbeat rate with respect to the change of the load around the exertion level estimated by the exertion level estimating unit; and a unit for controlling the load device to make the load come close to the level corresponding to the estimated physical strength.

The heartbeat rate of the electrocardiographic signal detected while gradually increasing the load is measured, a fluctuation of which is calculated, and the exertion level is estimated based on the heartbeat rate and the fluctuation of heartbeat rate intervals. The load of the load device is controlled to come around the estimated exertion level. Therefore, an exercise machine allowing a user to understand his/her own working capacity more precisely and hence to do appropriate exercise can be provided.

According to a still further aspect of the present invention, the physical strength evaluating method includes the steps of: gradually increasing a load of a load device; detecting by an electrocardiographic sensor an electrocardiographic signal under an increasing exertion load while the load is gradually increased; finding a heartbeat rate and a fluctuation of heartbeat rate intervals from the electrocardiographic signal detected; and estimating physical strength and an exertion level at the same time from the heartbeat rate and the fluctuation of heartbeat rate intervals thus obtained.

The electrocardiographic sensor detects the electrocardiographic signal corresponding to the increasing exertion load, and the heartbeat rate and the fluctuation of heartbeat rate intervals are obtained from the detected electrocardiographic signal. Based on thus obtained heartbeat rate and fluctuation of heartbeat rate intervals, the physical strength and the exertion level are estimated at the same time. Thus, a physical strength evaluating method capable of evaluating the physical strength and the exertion level with high precision in a short time period can be provided.

According to yet another aspect of the present invention, the pulse rate meter includes: a pulse rate sensor detecting a pulse rate signal produced by a heart; an alarm unit demanding a gradual increase of a pitch of exercise; an exertion level estimating unit estimating an exertion level based on the pulse rate signal detected by the pulse rate sensor while exercise is gradually intensified; and a unit for setting a pace based on the pitch of exercise corresponding to the exertion level estimated.

As the pulse rate meter can estimate the exertion level from the pulse rate signal detected while the pitch of exercise is gradually increased, it is possible to readily find an exertion level of an individual while he/she is engaged in exercise in the field.

BRIEF DESCRIPTION OF THE DRAWINGS

FIG. 6 is a flow chart illustrating an example of an exercise program corresponding to AT.

BEST MODE FOR CARRYING OUT THE INVENTION

Hereinafter, embodiments of the present invention will be described with reference to the drawings.

(1) First Embodiment

Figure 1:
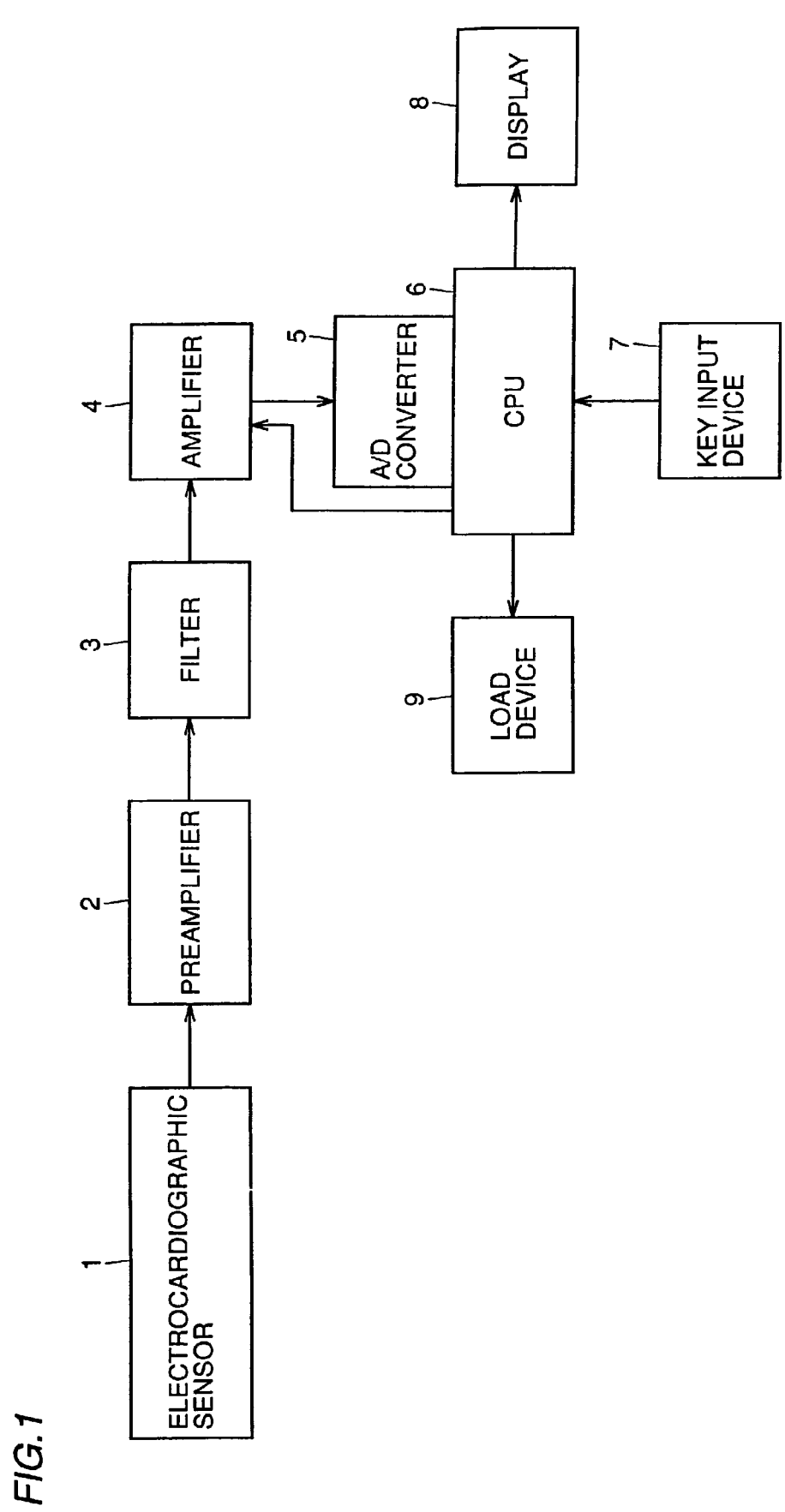
FIG. 1 is a block diagram showing a circuit configuration of a bicycle ergometer according to an embodiment of the present invention.

FIG. 1 is a block diagram showing a circuit configuration of a bicycle ergometer that is an example of the exercise machine according to the first embodiment of the present invention. This ergometer includes an electrocardiographic sensor 1 detecting an electrocardiographic signal; a preamplifier 2 amplifying the output signal; a filter 3 removing noise; an amplifier 4 further amplifying the electrocardiographic signal to an appropriate level, an A/D converter 5; a CPU 6 performing various kinds of processing; a key input device 7; a display 8; and a load device (applying a rotation load) 9.

Figure 2:
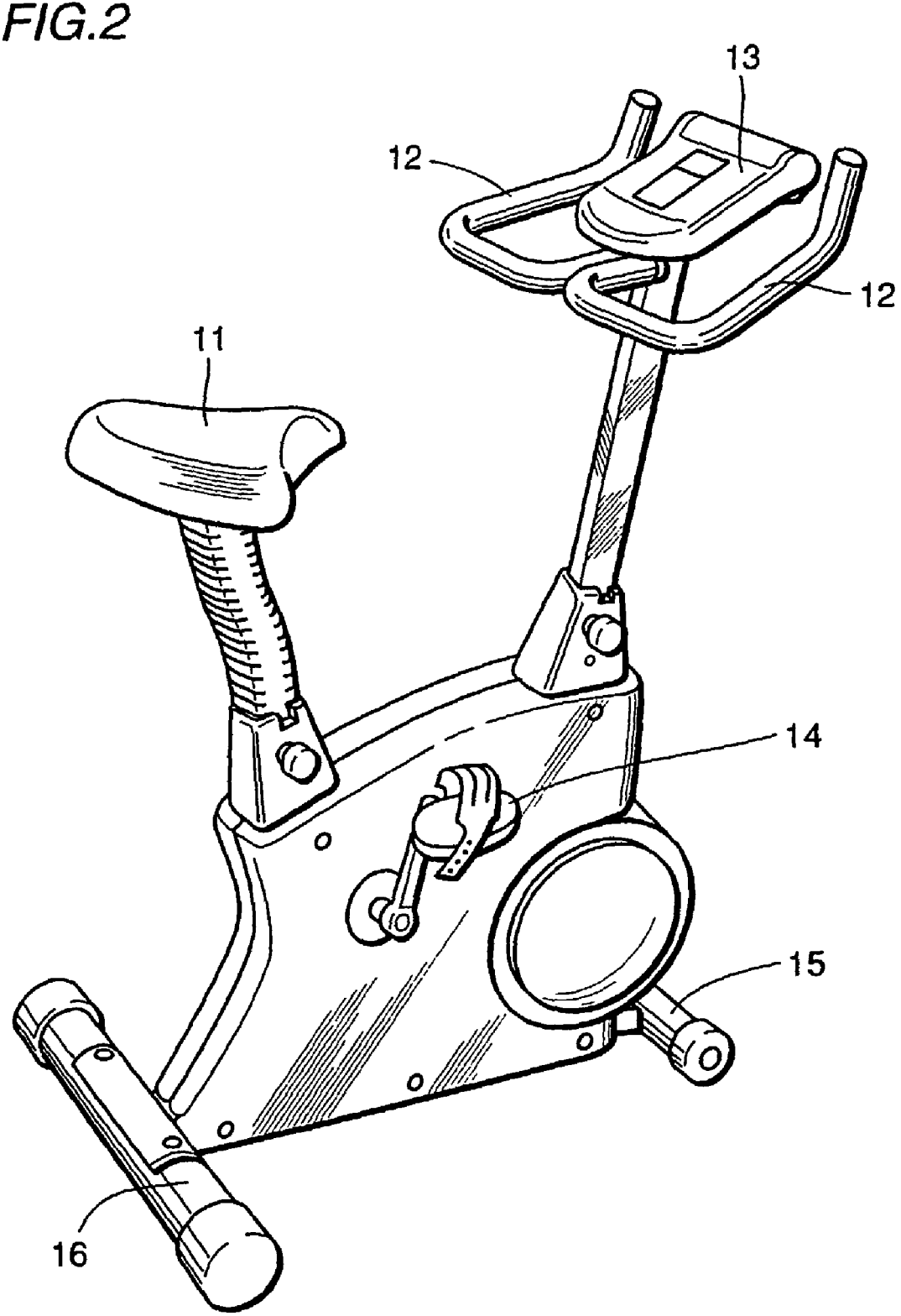
FIG. 2 is a perspective view of the bicycle ergometer.

FIG. 2 is a perspective view of the bicycle ergometer according to this embodiment. Referring to FIG. 2, the bicycle ergometer includes: a saddle 11; a handle 12; a manipulation unit 13; pedals 14; a front foot frame 15; and a hind foot frame 16. Manipulation unit 13 includes key input device 7 and display 8 (See FIG. 1). With this ergometer, a test subject (an exercising person) sits on saddle 11 and works pedals 14 to rotate them for exercise. Load device 9 applies a load to pedals 14 to give them weight corresponding to a degree of exertion intensity. For the greater load, the larger amount of exercise is naturally needed to rotate pedals 14 a fixed number of times. Electrodes of electrocardiographic sensor 1 are attached to the chest of the subject by means of a belt. The electrocardiographic to signal detected is transmitted by radio to manipulation unit 13 and other circuits for processing.

Figure 10:
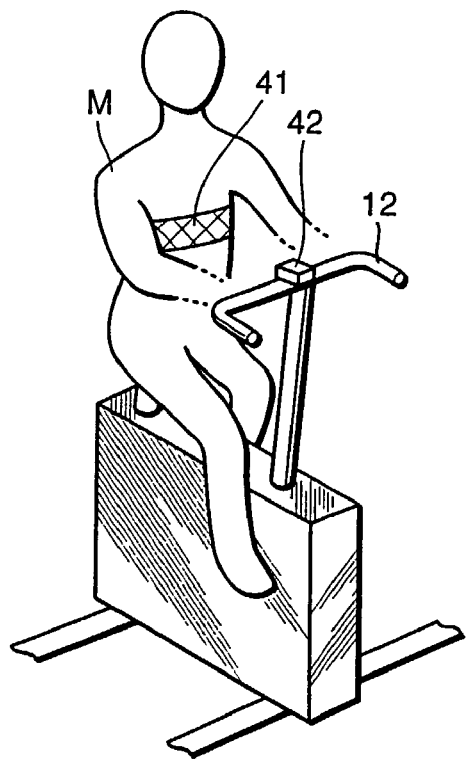
FIG. 10 shows, in a worn state, one of the electrocardiographic sensors being used in the bicycle ergometers of the first and second examples.

FIG. 10 illustrates an example of how electrocardiographic sensor 1 is worn. A chest belt 41 incorporating a pair of electrodes and a transmitter is worn around the chest of the subject M. Handle 12 incorporates a receiver (corresponding to manipulation unit 13 of FIG. 2) 42.

Figure 11:
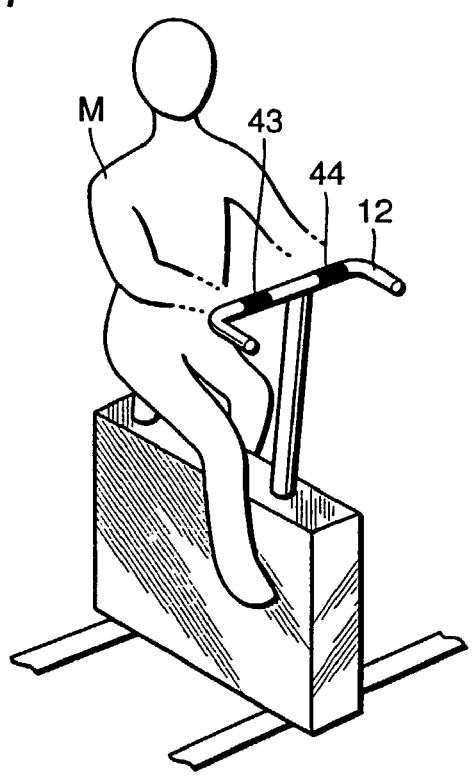
FIG. 11 shows another electrocardiographic sensor being used in the bicycle ergometer of the first example.

FIG. 11 shows another example of the electrocardiographic sensor for use with the bicycle ergometer. Electrodes 43, 44 for electrocardiographic detection are provided in handle 12. Gripping the handles, and hence, electrodes 43, 44 with respective hands enables the electrocardiographic detection. Electrodes 43, 44 are connected to the circuitry within the body of ergometer.

Figure 12:
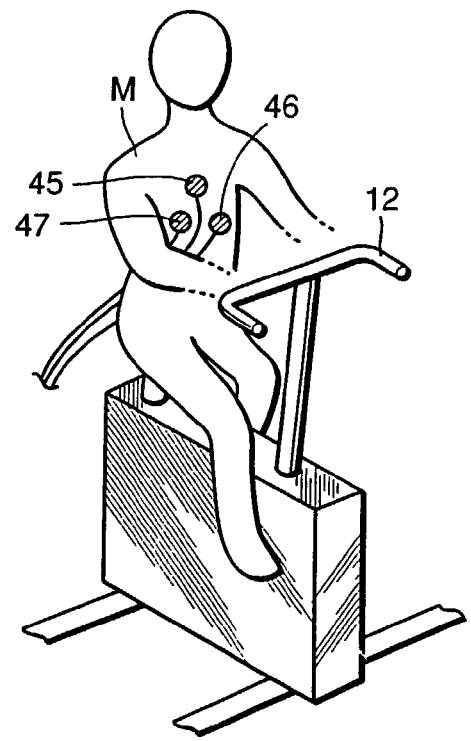
FIG. 12 shows yet another electrocardiographic sensor being used in the bicycle ergometers of the first and second examples.

FIG. 12 illustrates still another example of the electrocardiographic sensor used with the bicycle ergometer. Referring to FIG. 12, three electrodes 45, 46, 47 of G (ground),+ (plus) and − (minus), respectively, are attached to the chest of the exercising person M. This sensor is of a chest leads type with the electrodes being connected to the circuitry within the ergometer body by wire 48 for detection of the electrocardiographic signal.

Figure 13:
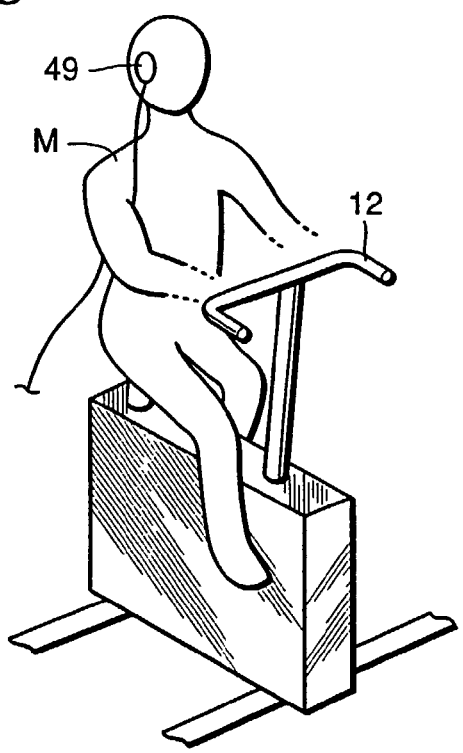
FIG. 13 shows, in a worn state, a pulse rate sensor being used in the bicycle ergometer according to the first embodiment.

FIG. 13 shows an example of a pulsation sensor for use with the bicycle ergometer. The pulsation sensor 49 is attached to an earlobe of the subject M for detection of pulsation.

In a conventional exercise machine such as an ergometer, an exercise program for weight reduction or enhancement of physical strength was determined based on the statistic data stating that the AT point as an example of exertion level should be around 55% of the maximum heartbeat rate (maximum exertion intensity) determined by age or the like having been input.

Figure 3:
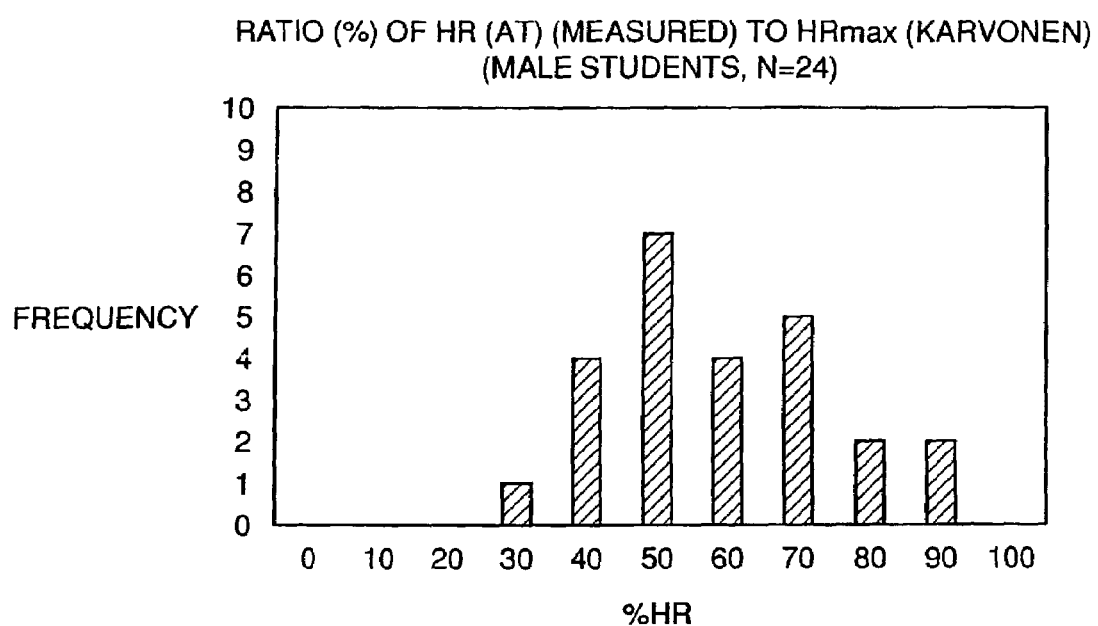
FIG. 3 illustrates distribution of anaerobic thresholds with respect to respective maximum heartbeat rates.

In practice, however, the actual measurement of AT represented in % as a ratio to the maximum heartbeat rate greatly differs from person to person, as shown in FIG. 3. FIG. 3 shows distribution of the AT measurements of 24 male students, with their respective maximum heartbeat rates being 100%. Thus, the exercise program based on the exertion intensity statistically determined in the conventional manner is not necessarily best suited for each person.

In the bicycle ergometer according to the present embodiment, in addition to the conventionally displayed physical strength level that is shown by estimating the maximum exertion intensity such as the maximum oxygen intake (maximum heartbeat rate), an AT as an example of exertion level is estimated at the same time from a fluctuation of heartbeat rate intervals, and is output for display as aerobic working capacity.

Figure 4:
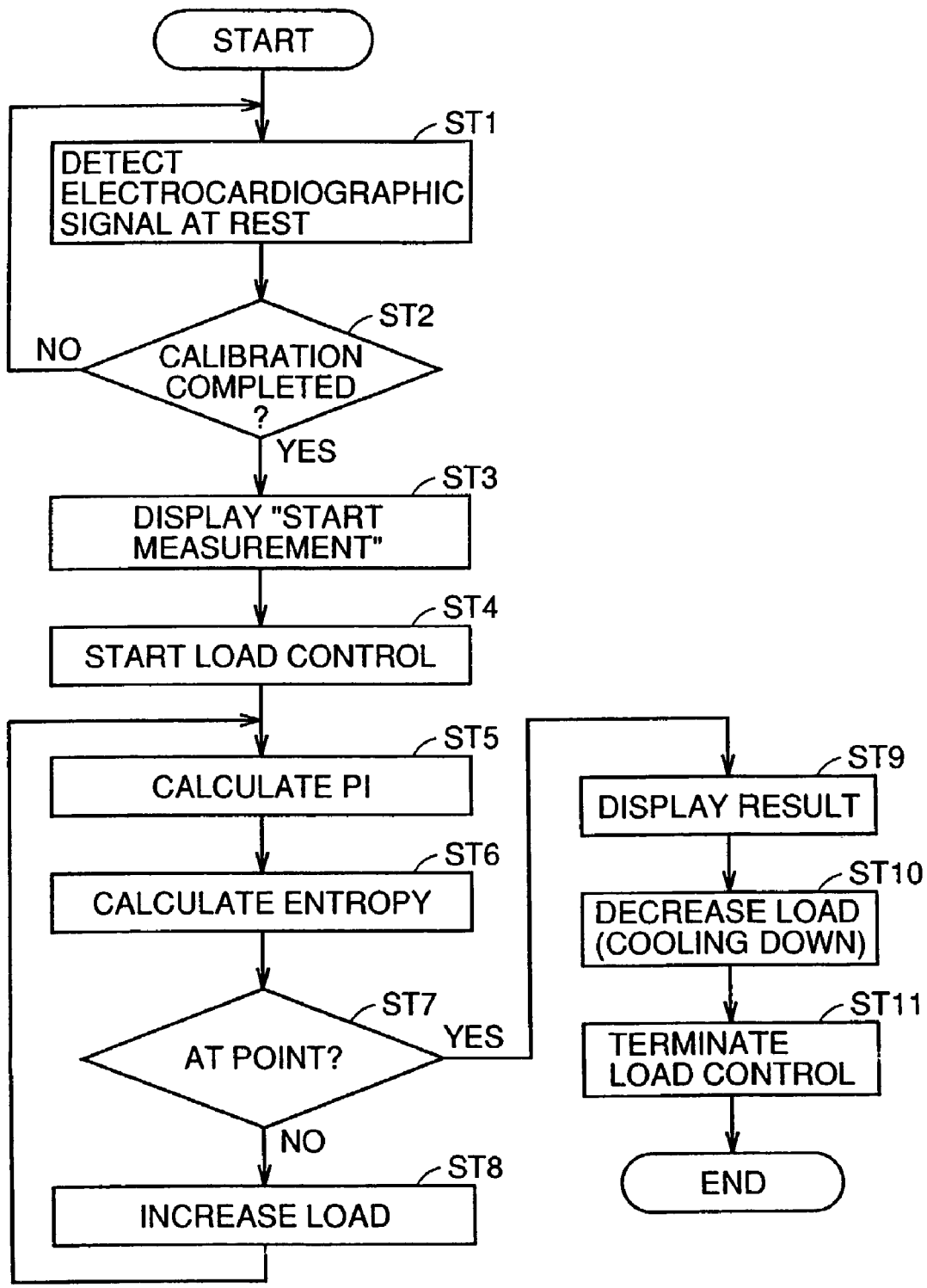
FIG. 4 is a flow chart illustrating a processing operation for AT estimation of the bicycle ergometer of a first example.

Now, the processing operation of the bicycle ergometer according to the present embodiment will be described with reference to the flow chart shown in FIG. 4. When measurement start key depress information is input from key input device 7 to CPU 6, the measurement is started. First, an electrocardiographic signal at rest is detected by electrocardiographic sensor 1 (step ST1; hereinafter "step" is not repeated). A calibration operation is performed so that this signal from electrocardiographic sensor 1 reaches a certain fixed level (ST2). To accomplish this calibration operation, a gain is adjusted at amplifier 4 according to a signal from CPU 6.

"Start measurement" is displayed on display 8 (ST3), and load control of load device 9 is started (ST4). As the load of load device 9, a ramp load of 15 W [watt] per minute is applied. The peak value of the electrocardiographic signal is detected to obtain RR interval data (one cycle of heartbeat). Using thus obtained RR data, PI (Percent Index) is calculated (ST5). Herein, the PI represents, in percentage, a ratio of a difference between the previous cycle and the current cycle to the previous cycle, which is calculated from the following expression:

$$PI(n)\% = \{RR(n) - RR(N+1)\}/RR(n) \times 100\%$$

Herein, this PI is called a fluctuation of heartbeat rate intervals.

From 128 pieces of this PI data, or at an interval of every two minutes, frequency distribution in percentage is calculated. From $P(i) = f(i)/f$, and according to the following expression (1), entropy H of the fluctuation of heartbeat rate intervals is calculated (ST6).

$$H = -\sum_i P(i) \log_2 P(i) \qquad (1)$$

Figure 5A:
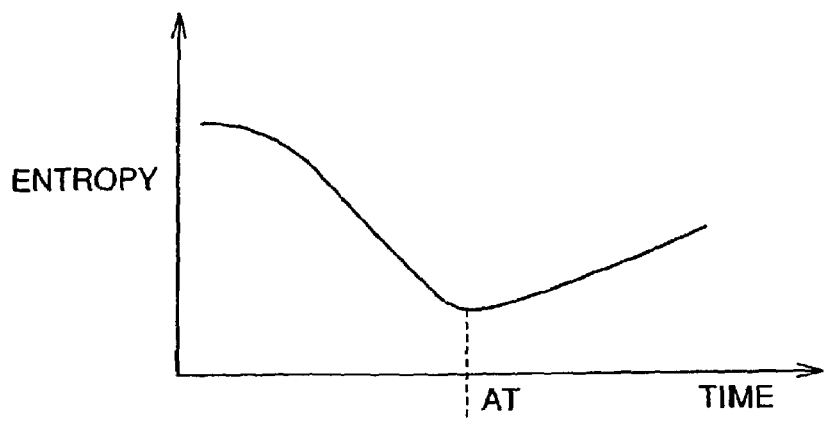
FIGS. 5A and 5B illustrate a gradual load increase by an exercise machine and an entropy change of fluctuation of heartbeat rate intervals.
Figure 5B:
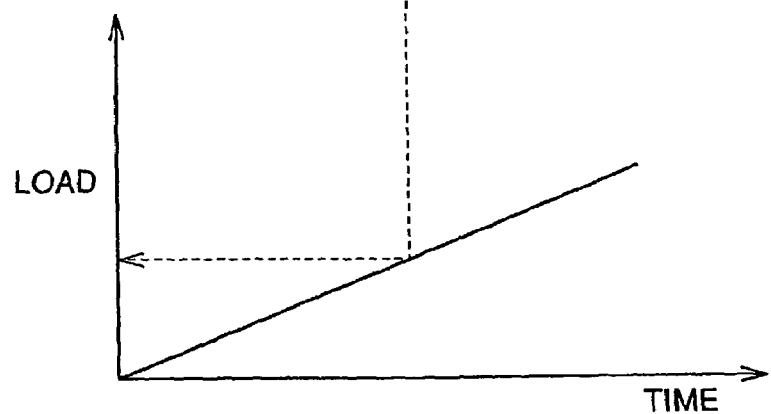

Thereafter, a decision is made whether the AT point is reached (ST7). As shown in FIGS. 5A and 5B, if the entropy decreases as the amount of exercise increases, the decision is NO. The load is thus increased gradually (ST8), while the PI value and entropy are calculated continuously (ST5, ST6). As shown in FIG. 5A, when the entropy reaches its polarization point (minimum point), the point is regarded as the AT point. Thus, the decision in ST7 is YES, and this result is displayed on display 8 (ST9). The result includes heartbeat rate (bPM), load intensity (W), time (min) or the like at the AT point. After the display of the result, the load is decreased for cooling down (ST10). After one minute of the cooling down, application of the load is stopped, and the control is terminated (ST11).

The bicycle ergometer according to the present embodiment has a capability to readily obtain the AT. Conventionally, the exertion intensity of the exercise program for weight reduction, enhancement of physical strength or the like was set as its ratio to the maximum heartbeat rate in percentage, e.g., 65% for weight reduction, and 75% for physical strength enhancement. Conversely, with the present embodiment, such exertion intensity can be set like 18% less or 18% greater than the AT point. Thus, it becomes possible to adjust the exertion intensity to conform to the exertion level of the individual.

Figure 6:
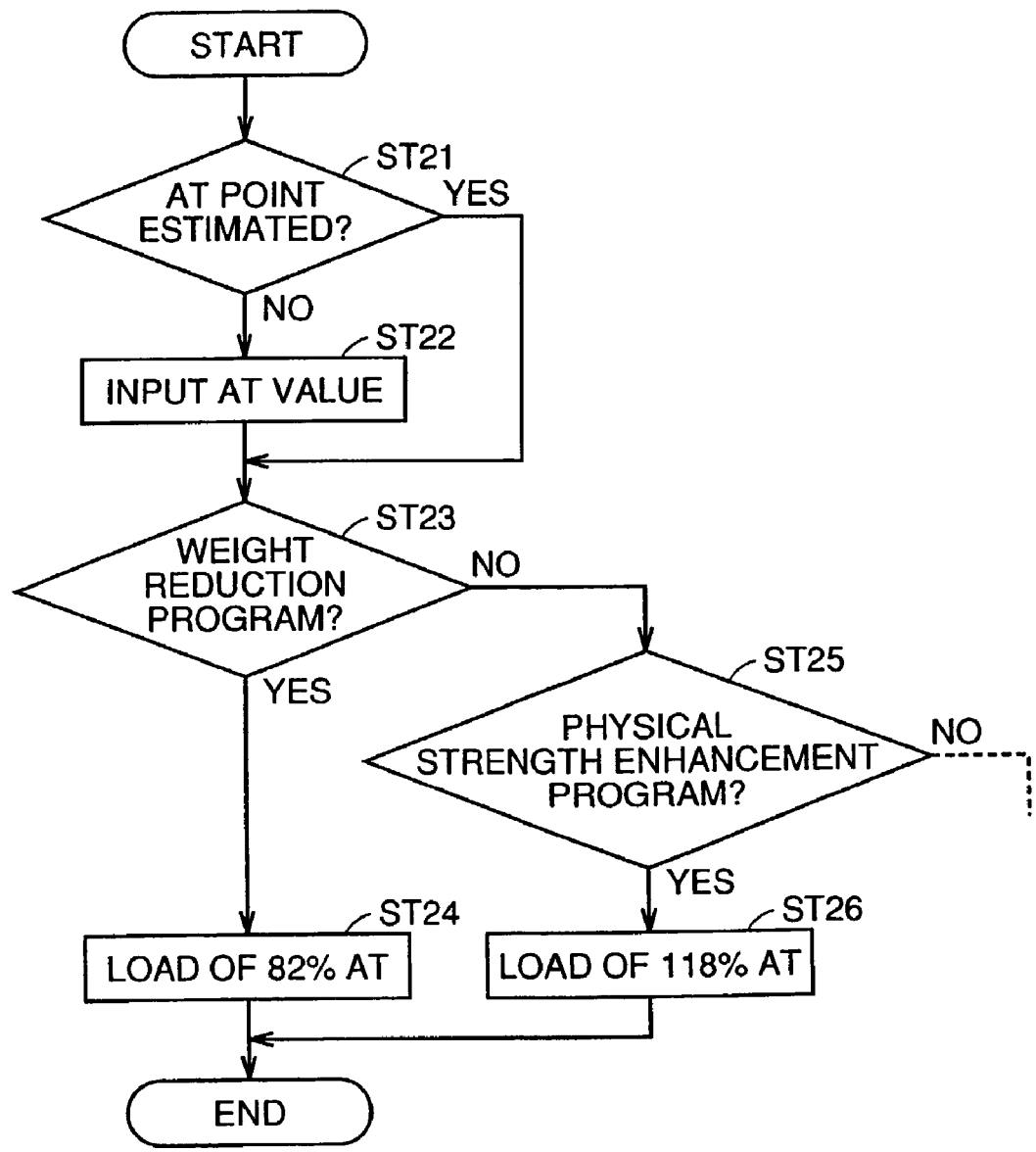

FIG. 6 is a flow chart showing an example of the process to determine exertion intensity from an estimated AT in the exercise machine according to the present embodiment. When the AT point is estimated (ST21), or, if the AT value of the specific person is already known and it is input via key input device 7 (ST22), then a determination is made whether a weight reduction program is designated (ST23). If YES, the load is set to 82% of the AT (ST24). If the weight reduction program is not designated, a determination is further made whether a physical strength enhancement program is designated (ST25). If YES, the load is set to 118% of the AT (ST26). If NO in ST25, control goes to still another process.

The bicycle ergometer according to the present embodiment is able to readily estimate both the maximum heartbeat rate (exertion intensity) and the AT. Thus, by showing in percentage a ratio of AT to the maximum heartbeat rate (exertion intensity) for each person, it is possible to show aerobic working capacity of the person in relation to a statistical average level. Thus, with this exercise machine having such a display output capability, not only the simple physical strength level, but also the aerobic working capacity can be output for display, so that a user can readily know his/her aerobic working capacity that has never been known with ease.

Another example of the ergometer according to the present embodiment will be described. The bicycle ergometer of this example has a circuit configuration similar to the one shown in FIG. 1, and again, in addition to the conventional display of physical strength level provided based on the estimation of the maximum exertion intensity such as the maximum oxygen intake (maximum heartbeat rate), it can estimate, at the same time, the AT from the fluctuation of heartbeat rate intervals, and output it for display as the aerobic working capacity.

Figure 7:
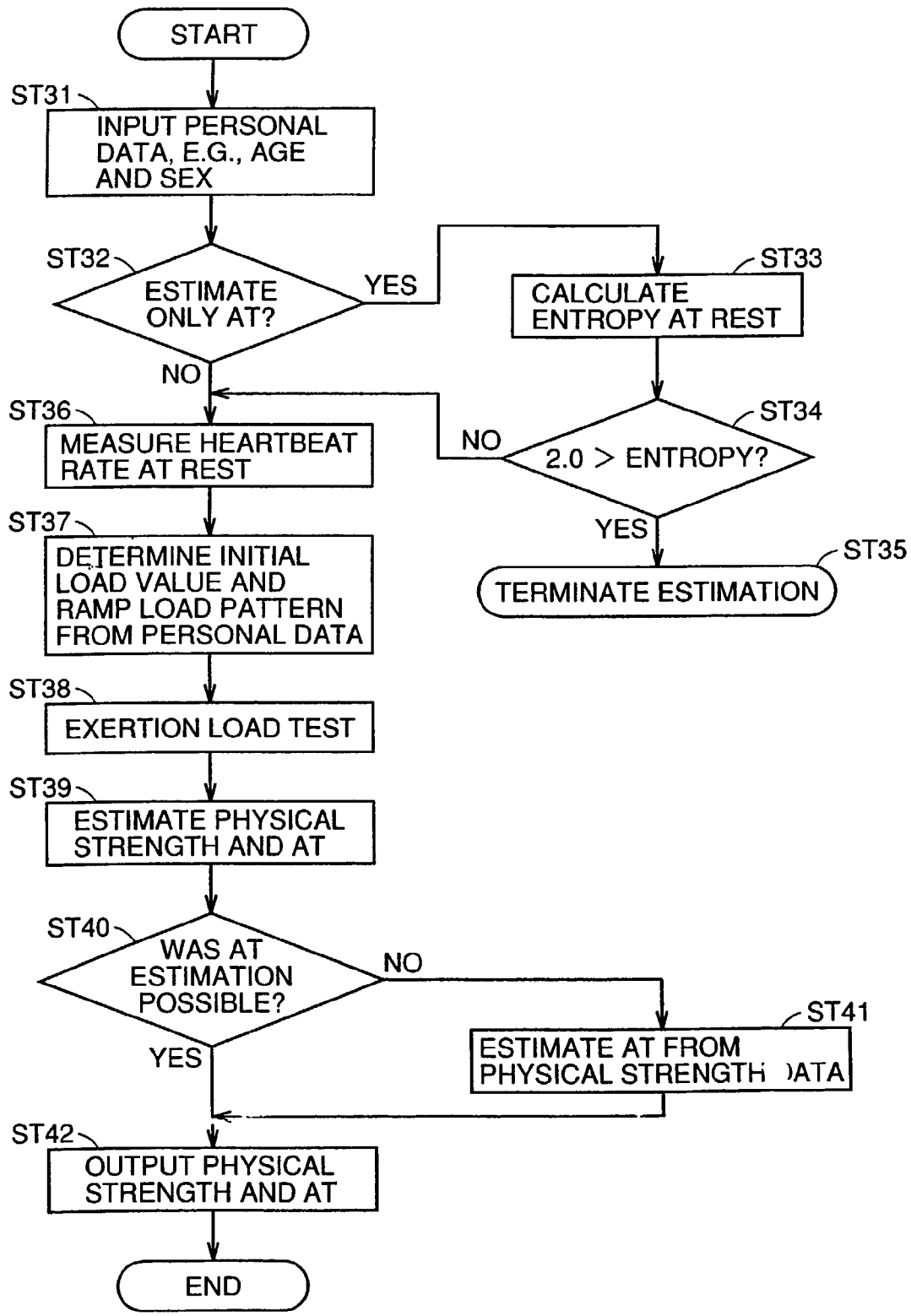
FIG. 7 is a flow chart illustrating a processing operation of the bicycle ergometer of a second example.

The entire operation of the exercise machine of this example will be described with reference to the flow chart shown in FIG. 7. Where the operation starts, personal data, such as age, sex or the like, is entered via key input device 7 (ST31). Next, a determination is made whether only the AT is to be estimated (ST32). If so with only the estimation of AT having been designated via key input device 7, entropy, of a heartbeat rate fluctuation at rest is calculated (ST33). If this entropy level is less than 2.0, it is determined that the AT estimation is impossible, and the estimation is terminated (ST35). This is because some test subjects exhibit almost no heartbeat rate fluctuation and hence a low entropy level at rest, and therefore, even if they are subjected to an exertion load test, the AT determination is expected to be very difficult. Thus, it is determined in advance that the AT estimation is impossible for them, such that they need not do unnecessary exercise.

For a test subject with the entropy level at least 2, or for a subject requesting estimation of both the AT and the physical strength, the heartbeat rate at rest is measured (ST36) and the exertion load test is conducted. At this time, an initial load value and an exertion load pattern of, e.g., gradually increasing ramp load are determined based on the personal data (ST37, ST38). Specifically, as it is inefficient to use the same pattern for persons with different physical strength levels, the personal data including age, sex or the like is referred to, and, for a subject with high physical strength level, initial values of the exertion load level and of a load increasing rate are set high. It should be understood, however, in order to maintain high precision in estimation, the load increasing rate exceeding a certain level, e.g., 40 W/min, is not applied in this case.

After the exertion load test, the physical strength and the AT level are estimated (ST39). Thereafter, a determination is made whether the AT estimation was possible (ST40). If the AT estimation was not possible, a statistical AT level, for example, 55% of the maximum heartbeat rate, is estimated from the estimated physical strength level (maximum heartbeat rate) (ST41), and output with the physical strength level (ST42). If it was possible to estimate the AT in ST40, thus estimated AT level and the physical strength level are likewise output (ST42).

Figure 8:
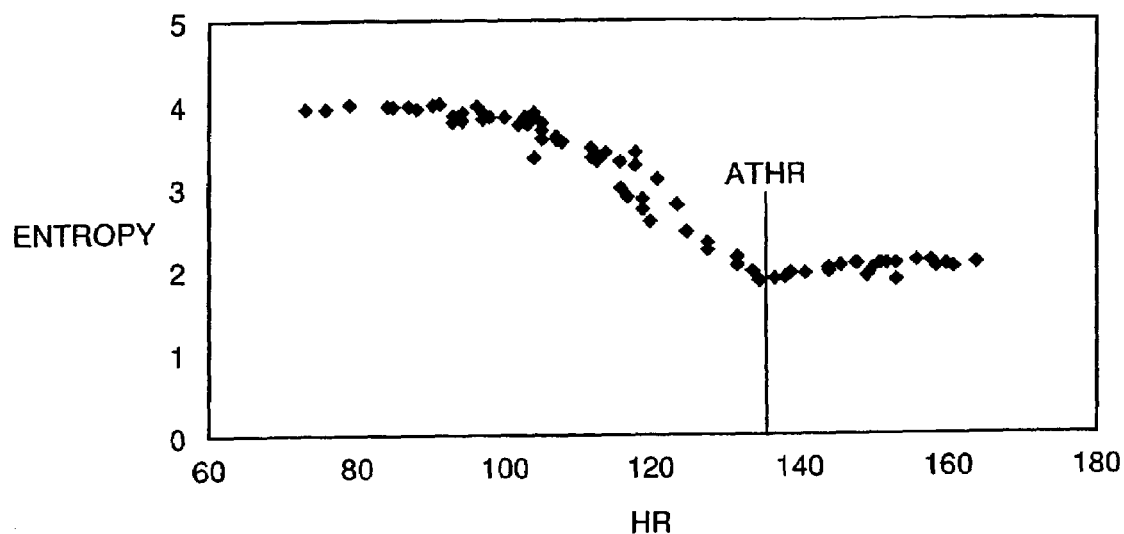
FIG. 8 shows a relation between the heartbeat rate and the entropy of fluctuation of heartbeat rate intervals while a load is gradually increased in the bicycle ergometer of the second example.

The above-described tests of physical strength and AT are conducted as follows. For the AT, the heartbeat rate interval data obtained by the exertion load test is used to find a relation between the heartbeat rate and the entropy of the fluctuation of heartbeat rate intervals as shown in FIG. 8. The AT is obtained as a heartbeat rate at the minimum point of the entropy.

To obtain the entropy of the heartbeat rate fluctuation, the PI is first calculated using the RR data and the following expression (2).

$$PI(n)\% = \{RR(n) - RR(n+1)\}/R(n) \times 100 \qquad (2)$$

From 128 pieces of such PI data, or at an interval of every two minutes, frequency distribution in percentage is calculated. $P(i) = fi/f$ is then found, and the entropy H is calculated using the expression (1) explained in conjunction with FIG. 4.

Figure 9:
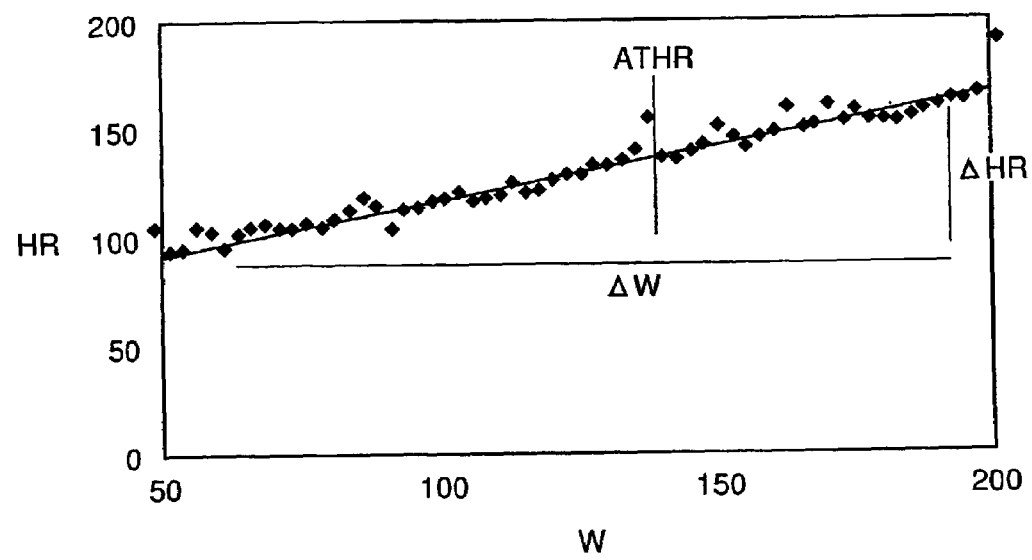
FIG. 9 shows a relation between the load and the heartbeat rate while the load is gradually increased in the bicycle ergometer of the second example.

Next, the physical strength level corresponding to the maximum exertion intensity is estimated based on the estimated AT, by finding a slope of the heartbeat rate change with respect to the exertion load level (W) within a predetermined range of, e.g., ±20 beats around the heartbeat rate at the estimated AT level, as shown in FIG. 9. If the AT estimation was not possible, a similar estimation is carried out in a range of ±20 beats around an index that is determined by {(200−age)−heartbeat rate at rest}×0.55+heartbeat rate at rest.

Accordingly, it is possible to estimate, from the electrocardiographic signal obtained at the exertion load test, the AT and the physical strength simultaneously and efficiently in a least possible time period.

Figure 14A:
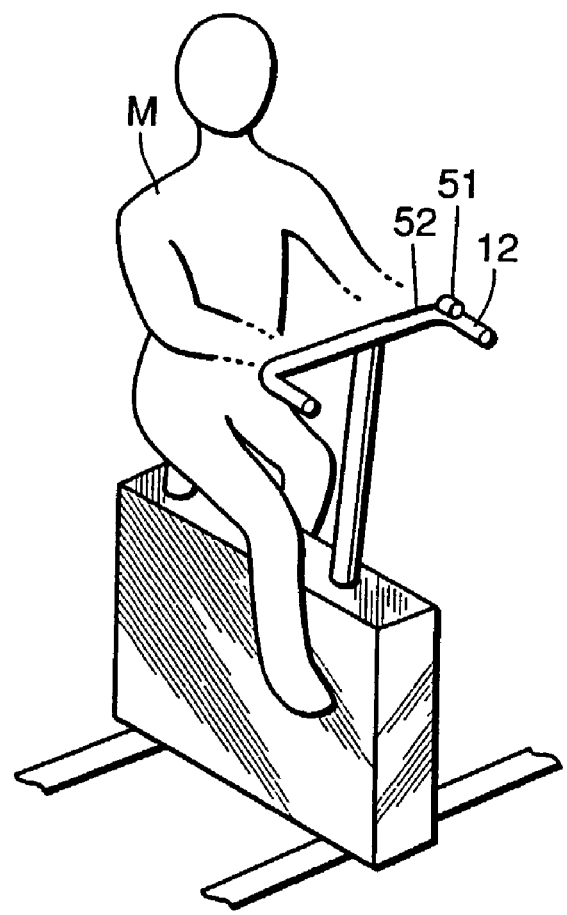
FIGS. 14A and 14B each show, in a worn state, a blood pressure gauge for finger being used in the bicycle ergometer according to the first embodiment.
Figure 14B:
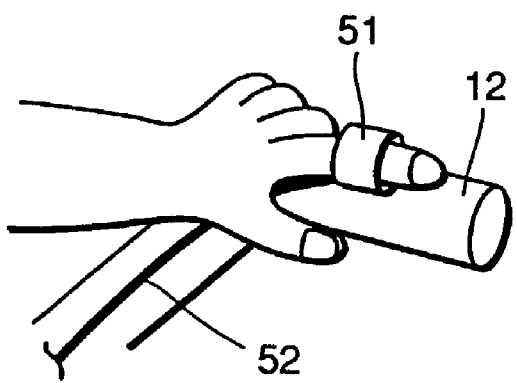
Figure 15A:
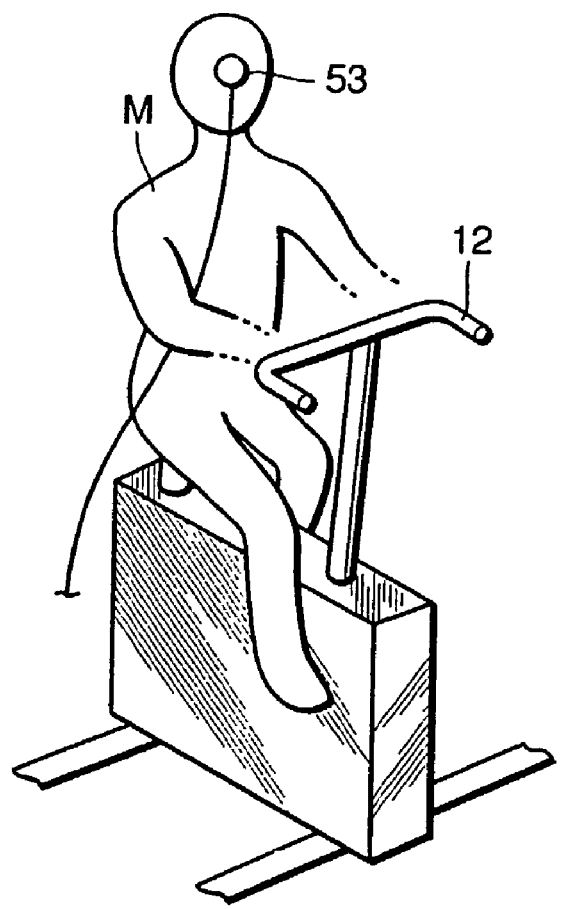
FIGS. 15A and 15B illustrate a way of detecting the breathing rate employed in the bicycle ergometer according to the first embodiment.
Figure 15B:
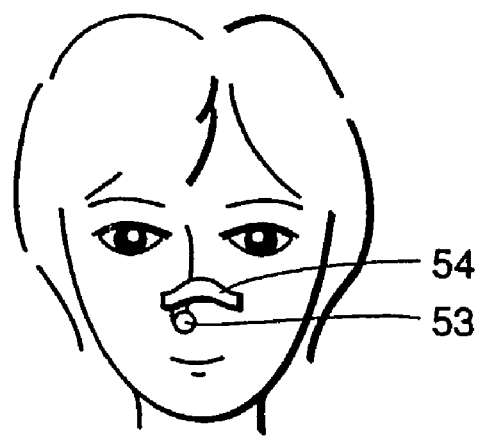

Each example described above has used the electrocardiographic signal measured by the electrocardiographic sensor as a physiological signal, and has employed the fluctuation of heartbeat rate intervals for estimation. Instead of the electrocardiographic signal, DP (Double Product) (blood pressure×heartbeat rate) or a breathing rate may be used as the physiological signal. The blood pressure during exercise can be measured, for example, by contacting handle 12 of the bicycle ergometer with a cuff 50 of a blood pressure gauge for finger, as shown in FIGS. 14A, 14B. In FIG. 14B, 51 denotes an air tube with a pulse signal line 52. The heartbeat rate can of course be measured by various kinds of electrocardiographic sensors as described above. The breathing rate is measured by attaching a thermistor 53 to the nose of the exercising person M. Thermistor 53, which is held, for example, by a tape 54 widening the nostril (see FIG. 15B), detects the temperature change due to breathing to measure the breathing rate.

Figure 16:
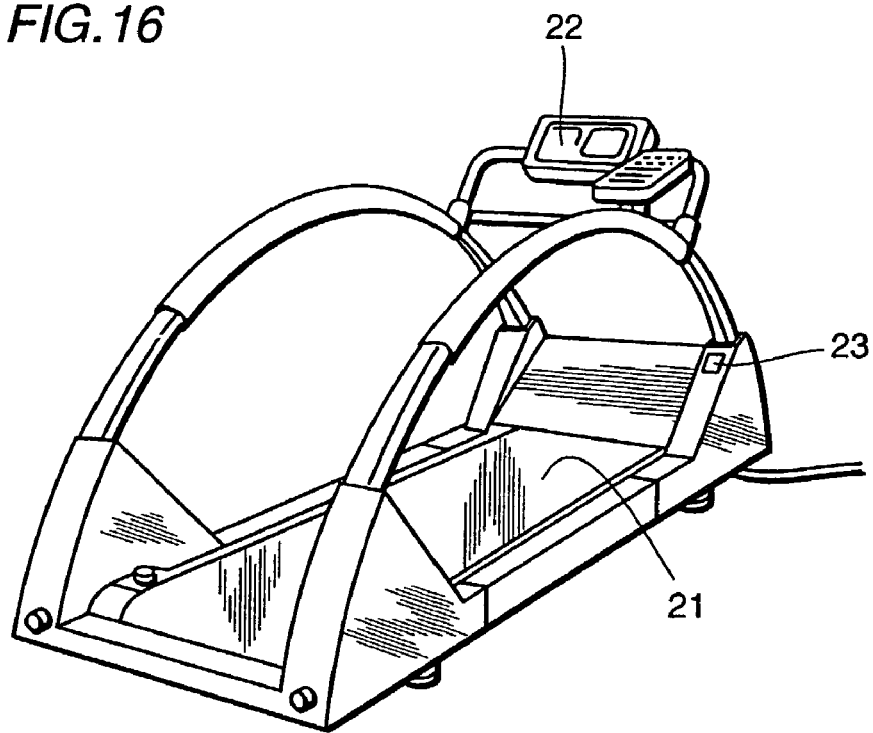
FIG. 16 is a perspective view of a treadmill as another example of the exercise machine implementing the present invention.
Figure 17:
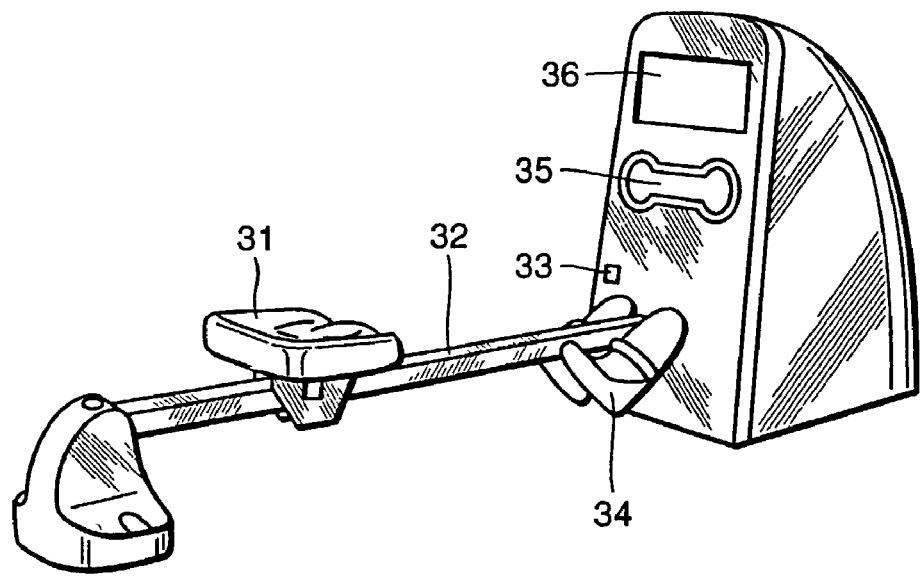
FIG. 17 shows a rowing ergometer as a further example of the exercise machine implementing the present invention.

In addition, although the bicycle ergometer has been used as the load device capable of changing a load in each example described above, the present invention is also applicable to a treadmill as shown in FIG. 16, a rowing ergometer in FIG. 17, or the like.

Referring to FIG. 16, a running belt is denoted by 21. A manipulation unit 22 includes a display portion, a key input portion and the like. When a power supply switch 23 is turned on, a built-in motor starts to move running belt 21. A person about to do exercise gets on this running belt 21, adjusts the moving rate of the belt, and starts running. In this treadmill, changing the number of rotation of the motor or the angle of inclination of the running belt can change the load.

The rowing ergometer shown in FIG. 17 includes a seat 31, a rail 32, a power supply switch 33, a foot rest 34, a bar 35 and a manipulation panel 36. A person about to do exercise sits on seat 31 and pulls the bar 35 with a rope attached thereto close to him/her and returns it back to its initial position repeatedly, so that he/she can do exercise feeling the load power incorporated. In this rowing ergometer, changing the tensile force of the bar that works to let it return to its initial position can alter the load.

(2) Second Embodiment

Hereinafter, the second embodiment of the present invention will be described. In the second embodiment, the anaerobic threshold is estimated utilizing a power of the fluctuation of heartbeat rate intervals. A bicycle ergometer being used and data being obtained from a test subject in the second embodiment are similar to those in the first embodiment.

Figure 18:
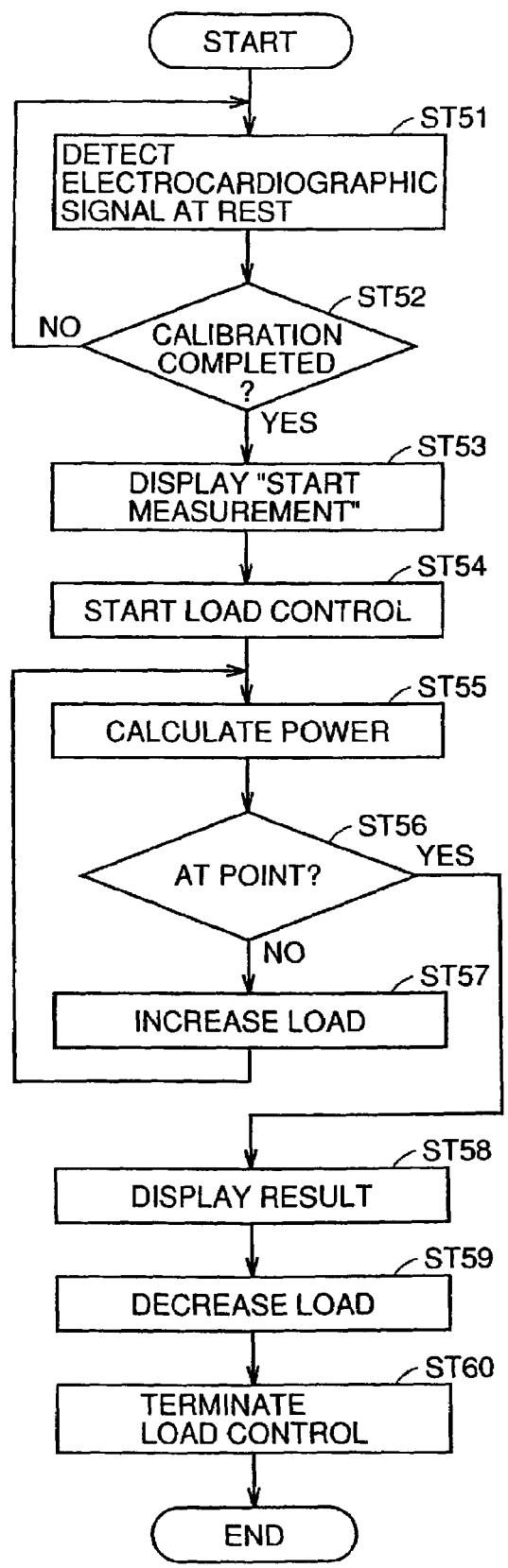
FIG. 18 is a flow chart showing contents of processing according to a second embodiment, for controlling a load by calculating a power of fluctuation of heartbeat rate intervals.

FIG. 18 is a flow chart showing contents of electrocardiographic signal processing according to the second embodiment. Referring to FIG. 18, in this embodiment, the electrocardiographic signal at rest is first detected (ST51). Calibration is then conducted, start of measurement is displayed, and load control is started (ST52-ST54). The steps heretofore are the same as in the first embodiment.

In the second embodiment, the peak of the electrocardiographic signal from eletrocardiographic sensor 1 is detected, and RR interval data (one cycle of the heartbeat rate) is calculated. Based on the RR interval data, a power is calculated using the following expression (3):

$$\text{power}(n)[ms^2] = \{RR(n-1) - RR(n)\}^2 \quad (3)$$

That is, the power is the square of the difference between the previous RR interval and the current RR interval. Herein, this power is called a power of the fluctuation of heartbeat rate intervals. The average value of this power data for 30 seconds, detected in 15 seconds, is used for estimation of the anaerobic threshold as an example of the exertion level.

Figure 19A:
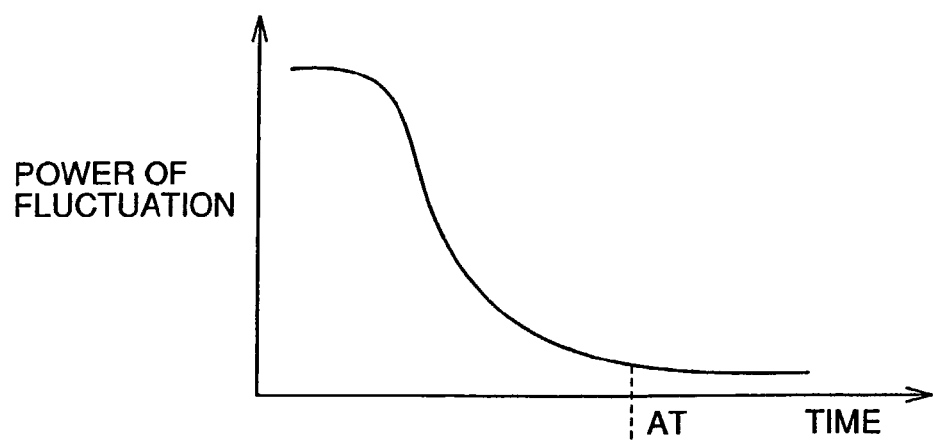
FIGS. 19A and 19B show a relation between the load and the power of fluctuation.
Figure 19B:
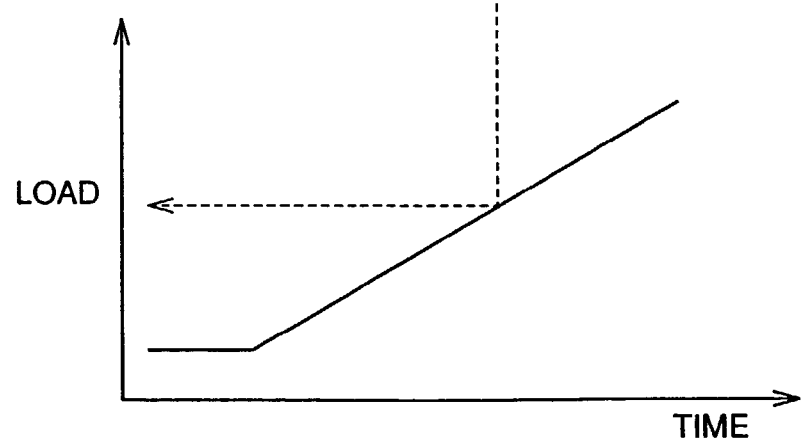

Next, in ST56, a determination is made whether the AT point has been reached. FIGS. 19A and 19B illustrate changes of the power of the fluctuation and the load over time. As shown in FIGS. 19A and 19B, the power of the fluctuation decreases to converge as the exertion load increases. The convergence point of the curved line showing the variation in the power of the fluctuation corresponds to the AT point. Herein, the convergence point is determined so when the power of the fluctuation becomes lower than a predetermined bottom value and when the difference from the previous power value (power (n−1)−power (n): slope of the curved line showing the variation of the fluctuation power) becomes lower than a predetermined reference value.

The load is increased until the AT point is obtained (ST57). When the anaerobic threshold point is reached (YES in ST56), the result is displayed, the load is decreased, and the load control is terminated (ST58-ST60). These steps are again the same as those in the first embodiment.

(3) Third Embodiment

Now, the third embodiment of the present invention will be described. A load of exercise may be controlled employing an oxygen intake, which is calculated from a load upon appearance of the anaerobic threshold detected by a method of either the first or the second embodiment. The oxygen intake (VO2) is calculated from the load at the time of appearance of the AT using a conversion formula, and VO2 per 1 kilogram of weight is obtained.

For example, when a person weighing 70 kg exercises with a bicycle ergometer and the AT appears at 100W, then the oxygen intake 13 calculated by the following expression (4):

$$VO2\ (ml/kg/min) = \text{load}(W) \div 0.232 \times 14.3 \div 5.0 \div \text{weight (kg)} \quad (4)$$

Herein, 0.232 means that the exercise efficiency of the bicycle ergometer is 23.2%. 14.3 is a conversion coefficient of 1 watt=14.3 cal/min. 5.0 is a conversion coefficient meaning that 5.0 kcal is consumed with the oxygen consumption of 1 litter. The operation result is as follows:

$$VO2\ (ml/kg/min) = 100 \div 0.232 \times 14.3 \div 5.0 \div 7.0 = 17.6$$

This means that the VO2 at the time of appearance of the anaerobic threshold is 17.6 (ml/kg/min).

As the AT of a healthy person generally appears at about 55% of the maximum oxygen intake (VO2max), the physical strength is measured by regarding the 55% of the standard value of VO2max at each age as the standard value of the anaerobic threshold.

(4) Fourth Embodiment

Now, the fourth embodiment of the present invention will be described. In the fourth embodiment, the method of detecting the anaerobic threshold as an example of the exertion level described in the first through third embodiments is applied to a pulse rate meter such as a heartbeat rate meter.

Figure 20:
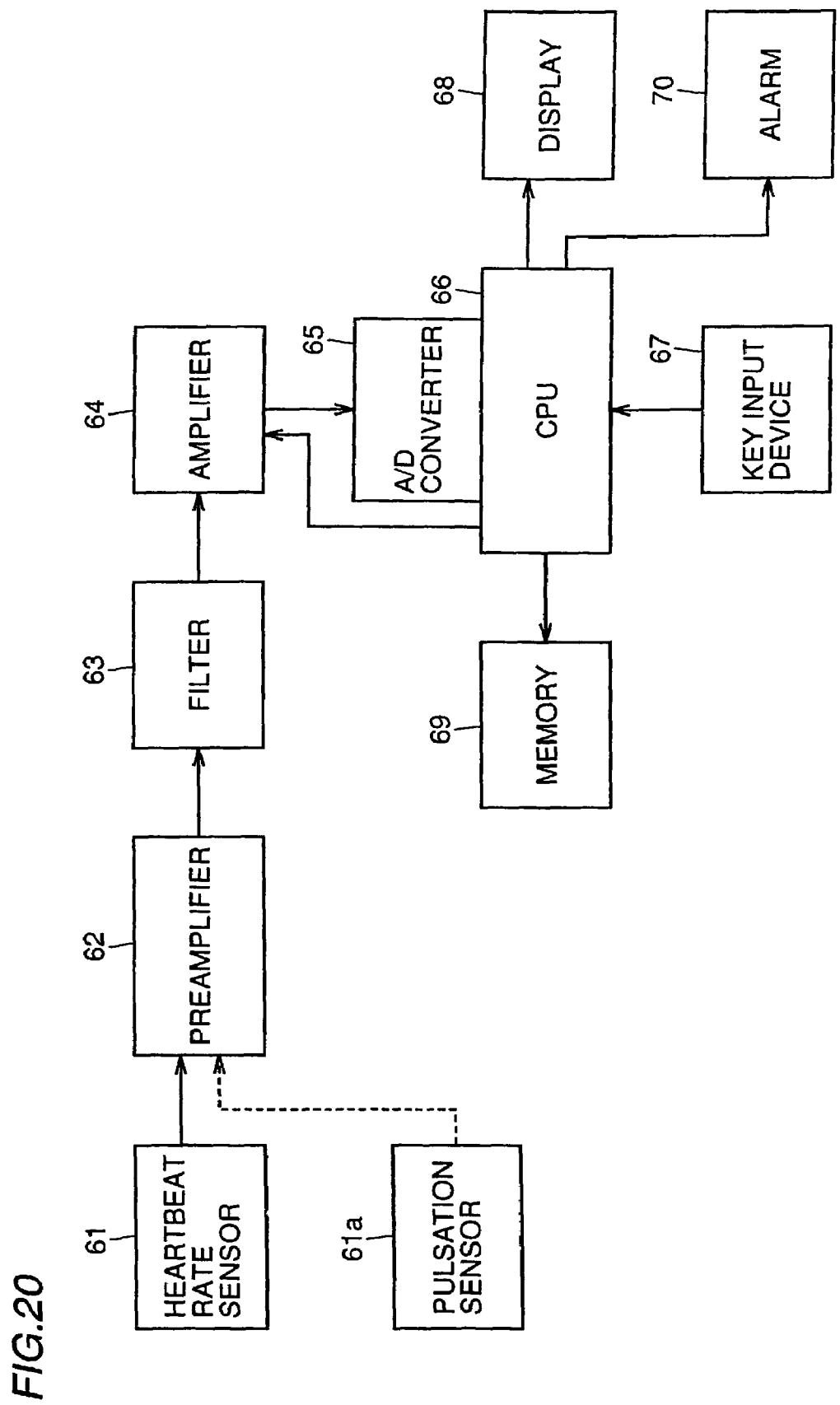
FIG. 20 is a block diagram showing a configuration of a pulse rate meter according to a fourth embodiment.

The configuration of the heartbeat rate meter according to the present embodiment is shown in FIG. 20. Referring to FIG. 20, the heartbeat rate meter of this embodiment includes: a heartbeat rate sensor 61; a preamplifier 62 amplifying a heartbeat rate signal detected by heartbeat rate sensor 61; a filter 63 removing noise; an amplifier 64 further amplifying the heartbeat rate signal amplified and filtered; an A/D converter 65; a CPU 66 performing various kinds of processing including estimation of an anaerobic threshold; a key input device 67; a display 68; a memory 69; and an alarm 70.

With the heartbeat rate meter according to the present embodiment, when the heartbeat rate reaches the AT level, alarm 70 notifies that it is at the anaerobic threshold level.

Display 68 displays the same information. Display 68 and alarm 70 also designate a pace of exercise at the anaerobic threshold level. Further, an exercise time with exertion intensity within a target zone that is set on the basis of the anaerobic threshold, and an exercise time with exertion intensity stronger or weaker than the exertion intensity in this range are calculated, and also displayed on display 68. The respective exercise times are stored in memory 69.

Figure 21:
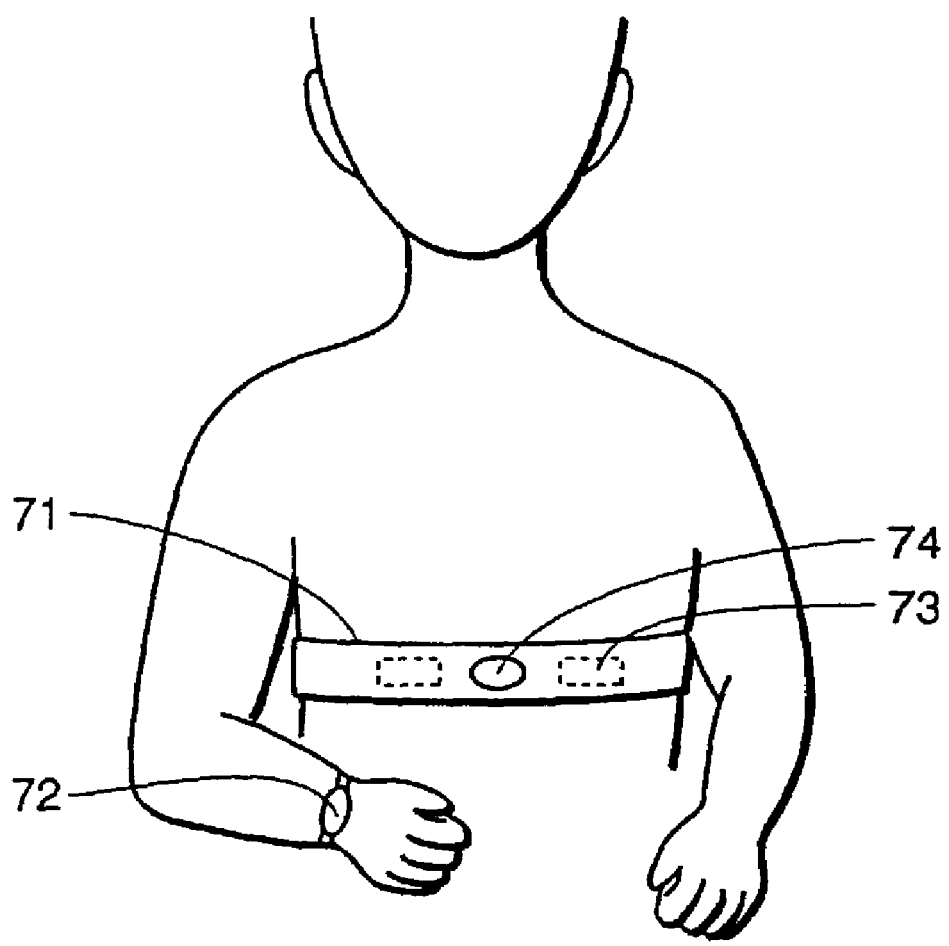
FIG. 21 illustrates how a heartbeat rate meter according to the fourth embodiment is worn by a test subject.

FIG. 21 shows, by way of example, how the heartbeat rate meter according to the present embodiment is worn. This heartbeat rate meter is formed of an enclosure 71 and a body 72 in the form of a wristwatch. Enclosure 71 includes electrocardiographic electrodes 73 and a transmitter 74, and body 72 receives the heartbeat rate signal transmitted. In terms of the circuit configuration, a transmitting unit and a receiving unit are provided anywhere between preamplifier 62 and A/D converter 65 shown in FIG. 20. Although body 72 is shown in the form of wristwatch, it may be a box having a manipulation panel or the like, dependent on a type of exercise.

Figure 22:
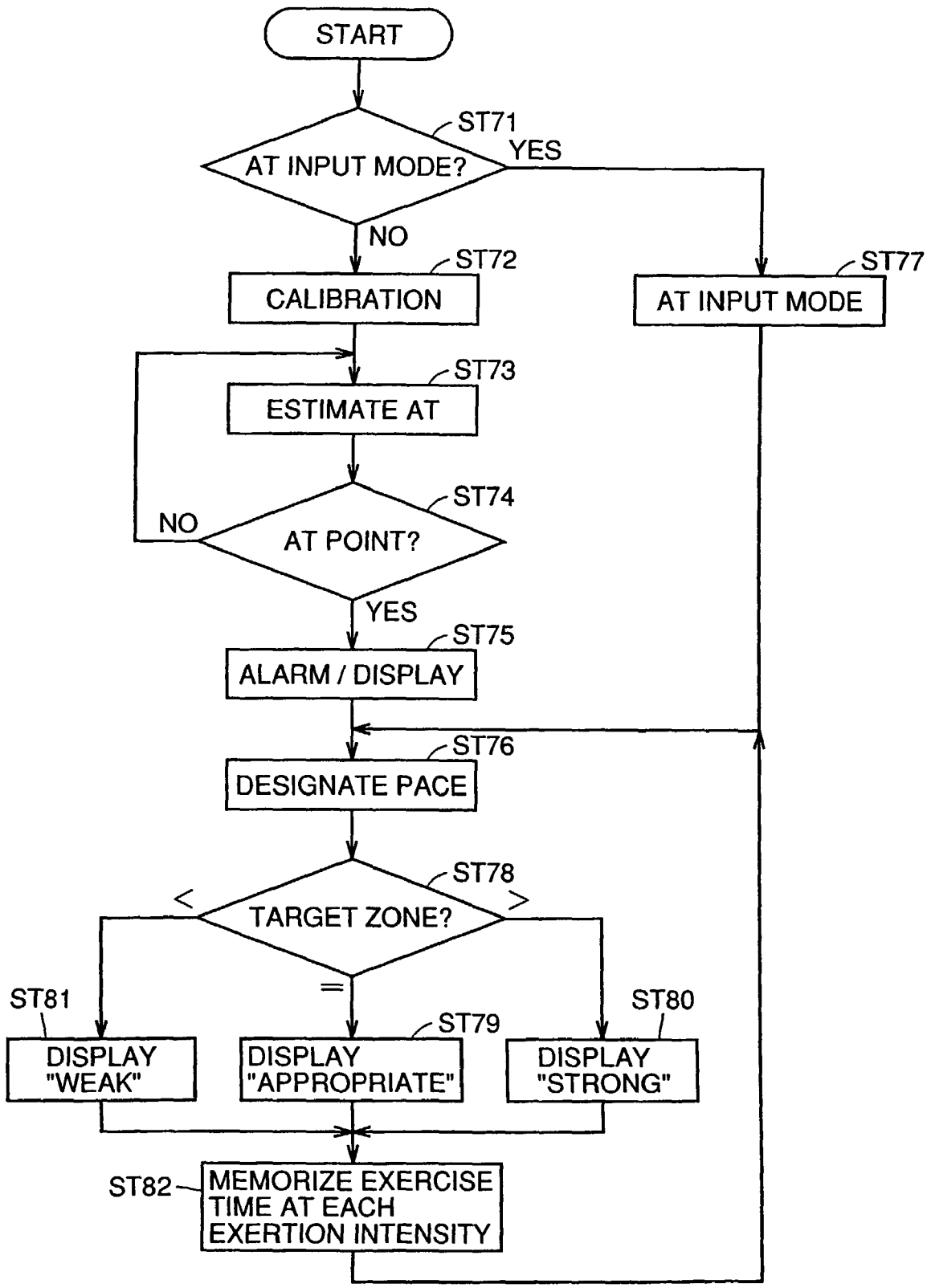
FIG. 22 is a flow chart showing a processing operation of the heartbeat rate meter according to the fourth embodiment.

Now, the processing operation of the heartbeat rate meter according to the present embodiment will be described with reference to the flow chart shown in FIG. 22. When start key depress information is input from key input device 7 to CPU 6, the measurement is started, and a determination is first made whether it is an AT input mode (ST71). If so, the AT pitch previously determined or the like is input, or read out from memory 69 (ST77). Thereafter, step ST76 and subsequent steps are carried out, which will be described later.

In ST71, if it is not the AT input mode and if the AT should be estimated, then a rest state is designated by alarm 70, and the heartbeat rate data at rest is input to CPU 66. At this time, calibration is performed such that the signal from heartbeat rate sensor 61 attains a prescribed fixed level (ST72).

Next, alarm 70 demands an exercise at a pitch corresponding to that of walking. The heartbeat rate data at this time is taken into CPU 6. The anaerobic threshold is then estimated (ST73). For this estimation of the anaerobic threshold, the pitch is gradually increased, and the corresponding heartbeat rate data are taken into CPU 66. The RR interval data is extracted, and then, the PI is calculated. Here, the PI is calculated by the expression (2) described above.

From 128 pieces of the PI data, or at an interval of every two minutes, frequency distribution in percentage is calculated. From $P(i)=f(i)/f$, according to the expression 2 as in the first embodiment, the minimum point of the entropy is detected and the anaerobic threshold is estimated (ST73, ST74).

The heartbeat rate and the pitch at this time are stored as the AT heartbeat rate and the AT pitch in memory 69, while they are displayed on display 68 and notified by alarm 70 (ST75).

Next, the AT pitch is used to set a pace of exercise. This pace of exercise is designated via display 68 and alarm 70 (ST76). A determination is then made whether the exercise is being done with the exertion intensity within a target zone that is set based on the AT pitch, or it is being done with the exertion intensity stronger or weaker than that in this range (ST78). According to the determination, "appropriate" (ST79), "strong" (ST80) or "weak" is displayed (ST81). Exercise times corresponding to respective exertion intensities are stored in memory 69 and displayed on display 68 (ST82). Alternatively, they may be only displayed on display 68 or only stored in memory 69.

In the heartbeat rate meter shown in FIG. 21, if a pulse rate sensor 61a is used in place of heartbeat rate sensor 61, it becomes a pulse rate meter, which can be utilized in the same manner as the heartbeat rate meter.

In the fourth embodiment, entropy is used for detection of the anaerobic threshold. Not limited thereto, however, the anaerobic threshold may also be detected employing the second or third embodiment.

Further, in the embodiments above, the anaerobic threshold has been used as the exertion level. Not limited thereto, however, the exertion level may of course be obtained employing any other data as long as it is based on the change of a physiological signal corresponding to the change of a load of the load device.

INDUSTRIAL APPLICABILITY

As explained above, the exercise machine according to the present invention estimates the anaerobic threshold based on an electrocardiographic signal corresponding to the change of a load of the load device, and controls the load based on the estimated value. Thus, an exercise machine permitting each person to do appropriate exercise in conformity with his/her own physical strength can be provided.

The invention claimed is:

1. An exercise machine, comprising:
    a load device gradually increasing a load over time;
    an electrocardiographic sensor detecting an electrocardiographic signal; a unit for measuring a heartbeat rate of the electrocardiographic signal detected while the load is gradually increased;
    a unit for calculating a fluctuation of heartbeat rate intervals in the electrocardiographic signal;
    an exertion level estimating unit estimating an exertion level based on said heartbeat rate and said fluctuation of heartbeat rate intervals; and
    a unit for controlling the load of the load device based on the exertion level estimated.

2. The exercise machine according to claim 1, wherein said exertion level is an anaerobic threshold.

* * * * *